(12) United States Patent
Jing

(10) Patent No.: US 10,874,846 B2
(45) Date of Patent: Dec. 29, 2020

(54) TRANSCUTANEOUS ELECTRICAL NERVE STIMULATION ELECTRODE NEEDLE AND TRANSCUTANEOUS ELECTRICAL NERVE STIMULATION DEVICE

(71) Applicants: BOE TECHNOLOGY GROUP CO., LTD., Beijing (CN); HEFEI BOE OPTOELECTRONICS TECHNOLOGY CO., LTD., Anhui (CN)

(72) Inventor: Yangkun Jing, Beijing (CN)

(73) Assignees: BOE TECHNOLOGY GROUP CO., LTD., Beijing (CN); HEFEI BOE OPTOELECTRONICS TECHNOLOGY CO., LTD., Anhui (CN)

(*) Notice: Subject to any disclaimer, the term of this patent is extended or adjusted under 35 U.S.C. 154(b) by 318 days.

(21) Appl. No.: 15/749,241

(22) PCT Filed: Jul. 27, 2017

(86) PCT No.: PCT/CN2017/094693
§ 371 (c)(1),
(2) Date: Jan. 31, 2018

(87) PCT Pub. No.: WO2018/049928
PCT Pub. Date: Mar. 22, 2018

(65) Prior Publication Data
US 2019/0030316 A1    Jan. 31, 2019

(30) Foreign Application Priority Data
Sep. 14, 2016 (CN) .......................... 2016 1 0825357

(51) Int. Cl.
*A61N 1/04* (2006.01)
*A61H 39/00* (2006.01)
(Continued)

(52) U.S. Cl.
CPC .......... *A61N 1/0456* (2013.01); *A61H 39/002* (2013.01); *A61H 39/086* (2013.01);
(Continued)

(58) Field of Classification Search
CPC .. A61N 1/0472; A61N 1/0476; A61N 1/0502; A61N 1/0551; A61N 1/08;
(Continued)

(56) References Cited

U.S. PATENT DOCUMENTS

2003/0153960 A1* 8/2003 Chornenky .......... A61N 1/0502
607/72

FOREIGN PATENT DOCUMENTS

CN         1390611 A      1/2003
CN         2555052 Y      6/2003
(Continued)

OTHER PUBLICATIONS

International Search Report and Written Opinion dated Oct. 27, 2017, for corresponding PCT Application No. PCT/CN2017/094693.
(Continued)

*Primary Examiner* — Catherine M Voorhees
*Assistant Examiner* — Roland Dinga
(74) *Attorney, Agent, or Firm* — Kinney & Lange, P.A.

(57) ABSTRACT

The present disclosure provides a TENS electrode needle and a TENS device. The TENS electrode needle includes: a needle handle having a first electrode and a second electrode for providing pulse current signals with different polarities are arranged; and at least one first needle body and at least one second needle body. Each of the first needle body and the second needle body includes a first end and a second end. The first end of the first needle body is electrically connected to the first electrode, and the first end of the second needle body is electrically connected to the second electrode, so as
(Continued)

to form an electrical field between the second end of the first needle body and the second end of the second needle body.

19 Claims, 3 Drawing Sheets

(51) Int. Cl.
  *A61H 39/08*    (2006.01)
  *A61N 1/36*     (2006.01)
  *A61N 1/05*     (2006.01)
  *A61N 1/08*     (2006.01)

(52) U.S. Cl.
  CPC .... *A61N 1/0492* (2013.01); *A61H 2201/0173* (2013.01); *A61H 2201/0192* (2013.01); *A61H 2201/0207* (2013.01); *A61H 2201/10* (2013.01); *A61H 2201/1207* (2013.01); *A61H 2201/169* (2013.01); *A61H 2201/50* (2013.01); *A61H 2230/105* (2013.01); *A61H 2230/505* (2013.01); *A61N 1/0472* (2013.01); *A61N 1/0476* (2013.01); *A61N 1/0502* (2013.01); *A61N 1/0551* (2013.01); *A61N 1/08* (2013.01); *A61N 1/3603* (2017.08); *A61N 1/36014* (2013.01); *A61N 1/36017* (2013.01); *A61N 1/36021* (2013.01)

(58) Field of Classification Search
  CPC ............ A61N 1/36014; A61N 1/36017; A61N 1/36021; A61N 1/3603; A61N 1/0492; A61N 1/086; A61N 1/002; A61N 1/04; A61N 1/56; A61H 2201/0173; A61H 2201/0192; A61H 2201/0207; A61H 2201/10; A61H 2201/1207; A61H 2201/169; A61H 2201/50; A61H 2230/105; A61H 2230/505
  See application file for complete search history.

(56) References Cited

FOREIGN PATENT DOCUMENTS

| | | |
|---|---|---|
| CN | 2561438 U | 7/2003 |
| CN | 1701823 A | 11/2005 |
| CN | 101926730 A | 12/2010 |
| CN | 206325120 U | 7/2017 |

OTHER PUBLICATIONS

First Chinese Office Action dated Dec. 26, 2017, for corresponding Chinese Application No. 201610825357.2.

* cited by examiner

TRANSCUTANEOUS ELECTRICAL NERVE STIMULATION ELECTRODE NEEDLE AND TRANSCUTANEOUS ELECTRICAL NERVE STIMULATION DEVICE

CROSS-REFERENCE TO RELATED APPLICATION

The present application is the U.S. national phase of PCT Application No. PCT/CN2017/094693 filed on Jul. 27, 2017, which claims a priority of the Chinese patent application No. 201610825357.2 filed on Sep. 14, 2016, which is incorporated herein by reference in its entirety.

TECHNICAL FIELD

The present disclosure relates to the field of medical equipment, in particular to a transcutaneous electrical nerve stimulation (TENS) electrode needle and a TENS device.

BACKGROUND

TENS (e.g., peripheral nerve coarse-fiber electrical stimulation) is an electrotherapy method for pain treatment by applying a specific low-frequency pulse current to a human body via skin. As compared with a conventional nerve stimulation therapy where a motor fiber is stimulated, the TENS is designed to stimulate a sensory fiber.

The so-called TENS is just "electrotherapy", which belongs to "naturopathy". The so-called "electrotherapy" refers to a therapeutic method of stimulating a nerve, muscle or cell through a continuous current at an appropriate strength and frequency, so as to enable a human body to generate morphine naturally, thereby to block transmission of pain information and relieve pain. The TENS is not limited to be used to relieve pain, and tissue regeneration may also be stimulated through a trace current similar to that generated by the human body. The tissue (or cell) regeneration relates to a series of chemical reactions using thermal energy and electric energy. In other words, a small amount of electric signals need to be provided as the energy desired for the cell regeneration. Microcurrent therapy, e.g., the TENS using a current characteristic, plays a very important role in lymph regeneration, wound healing and pain control.

Presently, a stimulating electrode of a TENS device is a patch electrode or an acupuncture needle which is capable of stimulating the nerve via an epidermis. For example, by applying the low-frequency pulse current to the acupuncture needle, an intensity of the electrode stimulation is increased through a tip of the acupuncture needle.

However, by applying the low-frequency pulse current to the acupuncture needle through a driver circuit, usually a unidirectional pulse (i.e., a single-polarity pulse) current is generated. This single-polarity pulse current may cause electrochemical damage to the human tissue, and even disturb physiological balance in the human body, e.g., an irreversible change in sodium and potassium in the human body may occur. In addition, the single-polarity pulse current may also be delivered through the tissue around the acupuncture needle, and at this time, a magnitude of the pulse current applied to the acupuncture needle may be limited. Further, it is necessary to apply a very small current, because a skin injury and muscle cramp may occur due to an excessive current, and even the acupuncture needle may be broken internally. In the case that the current is too small, a resultant therapeutic effect may be poor. Furthermore, voltages or currents applied to different persons may vary greatly.

SUMMARY

An object of the present disclosure is to provide a TENS electrode needle and a TENS device, so as to improve adaptability of the human body to the current as well as therapeutic effect.

In one aspect, the present disclosure provides in some embodiments a TENS electrode needle, including: a needle handle having a first electrode and a second electrode for providing pulse current signals with different polarities are arranged; and at least one first needle body and at least one second needle body. Each of the first needle body and the second needle body includes a first end and a second end. The first end of the first needle body is electrically connected to the first electrode, and the first end of the second needle body is electrically connected to the second electrode, so as to form an electrical field between the second end of the first needle body and the second end of the second needle body.

Optionally, a length of the first needle body is greater than a length of the second needle body.

Optionally, the second end of the first needle body is of a pointed shape for piercing into the skin; and the second end of the second needle body includes an electrode ring attached onto a surface of the skin, and the first needle body is inserted through the electrode ring, so as to form the electrical field between the second end of the first needle body and the electrode ring of the second needle body.

Optionally, a length of the first needle body is about the same as that of the second needle body, and each of the second end of the first needle body and the second end of the second needle body is of a pointed shape.

Optionally, at least two groups of needle bodies are arranged on the needle handle, and each group includes one of the at least one first needle body and one of the at least one second needle body.

Optionally, orthographic projections of the at least two groups of needle bodies onto a plane perpendicular to the needle handle form vertices of a polygon.

Optionally, the polygon includes a convex polygon.

Optionally, the at least two groups of needle bodies includes two groups of needle bodies that are arranged on the needle handle, and orthographic projections of the two groups of needle bodies onto the plane perpendicular to the needle handle form vertices of a diamond.

Optionally, orthographic projections of the first needle body and the second needle body belonging to a same group onto the plane perpendicular to the needle handle form a pair of nonadjacent vertices of the polygon.

Optionally, orthographic projections of two needle bodies in the at least two groups onto the plane perpendicular to the needle handle, which form two adjacent vertices of the polygon, are spaced apart from each other at a distance in a range of about 0.2 mm to about 2 mm.

Optionally, the at least one first needle body comprises two first needle bodies and the at least one second needle body comprises one second needle body, the two first needle bodies and the second needle body are arranged on the needle handle, and a distance between the second needle body and any one of the two first needle bodies is smaller than a distance between the two first needle bodies.

Optionally, a distance between any one of the at least one first needle body and any one of the at least one second needle body ranges from about 0.2 mm to about 2 mm.

Optionally, the first needle body has a resistance different from the second needle body.

Optionally, at least one of the first needle body and the second needle body is arranged on the needle handle through a length adjustment mechanism, so as to adjust a length of the at least one of the first needle body and the second needle body extending out of the needle handle.

Optionally, the length adjustment mechanism includes: a movement passage arranged within the needle handle; a sliding block arranged within the movement passage, the first end of the at least one of the first needle body and the second needle body extending into the movement passage and being connected to the sliding block; and a delimiting mechanism configured to define a position of the sliding block.

Optionally, an electromagnetic coil is wound onto the needle handle, and two ends of the electromagnetic coil are electrically connected to the first electrode and the second electrode respectively.

In another aspect, the present disclosure provides in some embodiment a TENS device, including: a pulse signal generation mechanism having two output ends for outputting pulse current signals with different polarities; and any one of the above-mentioned TENS electrode needles, wherein the first electrode and the second electrode in the needle handle of the TENS electrode needle are electrically connected to the two output ends of the pulse signal generation mechanism respectively.

Optionally, the pulse signal generation mechanism includes: a power source configured to provide an alternate current; a rectifier controller connected to the power source and configured to output a sinusoidal current; a control unit connected to the rectifier controller and configured to control an output state of the sinusoidal current from the rectifier controller, wherein the output state includes an output frequency and a size of the sinusoidal current; and a pulse signal generator connected to the rectifier controller and configured to receive the sinusoidal current from the rectifier controller and generate the pulse current signals.

Optionally, the pulse signal generation mechanism further includes an obtaining unit configured to obtain feedback information of a patient stimulated by a current predetermined pulse current signal, and the control unit is further connected to the obtaining unit and configured to control the output state of the sinusoidal current from the rectifier controller in accordance with the feedback information obtained by the obtaining unit.

Optionally, the obtaining unit includes: a brain wave monitor configured to obtain a brain wave signal of the patient stimulated by the current predetermined pulse current signal, generate a first feedback signal and transmit the first feedback signal to the control unit; and/or an infrared camera tube configured to obtain a state of a skin surface of the patient stimulated by the current predetermined pulse current signal at a position where the TENS electrode needle is located, generate a second feedback signal and transmit the second feedback signal to the control unit.

According to the embodiments of the present disclosure, the TENS electrode needle is provided with at least two needle bodies for providing the pulse current signals with different polarities. Through the two needle bodies, it is able to release the current in time and provide a relatively short duration of electrical stimulation, thereby to improve the adaptability of a human body to the current without causing any undesired stimulation to other part(s) of the human body. As compared with a stimulation mode in the related art where a unidirectional pulse current is used, in the embodiments of the present disclosure, it is able to increase the current, thereby to improve the therapeutic effect.

DETAILED DESCRIPTION

Figure 1:
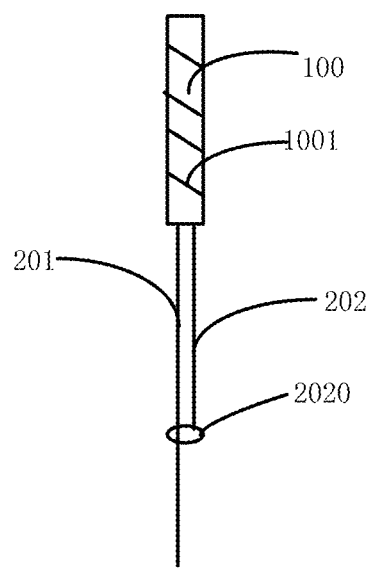
FIG. 1 is a schematic view showing a TENS electrode needle according to some embodiments of the present disclosure.

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

In the related art, the electrical stimulation is performed by a TENS device using a unidirectional pulse signal, resulting in physical discomfort and an insufficient therapeutic effect. An object of the present disclosure is to provide a TENS device, so as to improve the adaptability of a human body to the current as well as a therapeutic effect.

As shown in FIGS. 1 to 5, the present disclosure provides in some embodiments a TENS electrode needle, which includes: a needle handle 100 having a first electrode and a second electrode for providing pulse current signals with different polarities are arranged; and at least one first needle body 201 and at least one second needle body 202 connected to the needle handle 100. Each of the first needle body 201 and the second needle body 202 includes a first end and a second end. The first end of the first needle body 201 is electrically connected to the first electrode, and the first end of the second needle body 202 is electrically connected to the second electrode, so as to form an electrical field between the second end of the first needle body 201 and the second end of the second needle body 202.

Optionally, the at least one first needle body 201 and the at least one second needle body 202 may besecured onto the needle handle 100, or flexibly connected to the needle handle 100, e.g., the needle handle 100 may be detachably connected to the needle bodies. One or more of the needle bodies may also be arranged on the needle handle 100 through an adjustment mechanism, so as to adjust a length of the needle body extending out of the needle handle 100.

Optionally, a distance between any one of the at least one first needle body 201 and any one of the at least one second needle body 202 is within a certain range, e.g., 0.2 mm to 2 mm. Of course, a distance between any one of the at least one first needle body 201 and a second needle body arranged adjacent to (or farthest away from) the first needle body may be within a certain range. It should be appreciated that, the distance between any two of the needle bodies will not be particularly defined herein.

In the embodiments of the present disclosure, the TENS electrode needle is provided with at least two needle bodies, i.e., the first needle body 201 and the second needle body 202, for providing the pulse current signals with different polarities. A pulse generator may generate a pulse current at a certain period, and the pulse current flows into the first electrode in the needle handle 100 and out of the second electrode. In use, the second end of at least one of the first needle body 201 and the second needle body 202 may be pierced into under the epidermis. At this time, a short-range closed-loop micro electric field may be formed between the second ends of the two needle bodies arranged very close to each other, so as to change a micro electric field at an acupuncture point, thereby stimulating the relevant acupuncture point.

Based on a principle of controlling a bioelectric potential, a potential of a nerve may change under the effect of the short-range micro electric field. For example, a matrix-form wave may be obtained in accordance with a certain nervous wave (e.g., a wave) so as to stimulate the nerve, and a duration of the matrix-form wave may be adjusted so as to control the endurance of the human body to the electric field. The matrix-form wave may vary greatly, so it is able to achieve the effective stimulation. For example, the high-potential stimulation may be used to achieve a desired effect, and meanwhile the duration of the high-potential stimulation is very short, so it is able ensure the endurance of the human body to the electric field. In addition, a wavelength of the matrix-form wave may vary in a way similar to a wavelength of a certain music wave, i.e., the electric pulse may be generated in accordance with the music wave, so as to stimulate the nerve in a delight and effective manner.

In the embodiments of the present disclosure, in the case that the short-range electric field is adopted, a short current loop may be formed after the stimulation, so it is able to release the current after the stimulation and effectively prevent the nerve from being stimulated for a long time period. In addition, the heart, brain and any other part(s) of a person are not directly stimulated by the current, so it is able to reduce the damage to the human body, and increase the security.

In addition, through the acupuncture point stimulation using the short-range closed-loop electric field, it is able to reduce the electrochemical damage to a nerve fiber. Through the at least two electrodes, it is able to ensure an overall charge balance of the pulse applied to an individual electrode, i.e., ensure that an overall amount of the static charges passing through the nerve fiber is zero. Further, through the acupuncture point stimulation using the short-range closed-loop electric field, it is able to reduce the occurrence of nerve fatigue during the stimulation, stimulate the nerve in an oriented manner, and control the change in nervous excitation. Merely the beneficial nerve stimulation may provide a beneficial therapeutic effect. The nerve stimulation may not only adjust a pain sense, but also improve the hormone secretion. To be specific, the hypothalamus may be stimulated, so as to adjust the hormone secretion, thereby to generally adjust a health condition. Furthermore, through the stimulation in an oriented manner, it is able to suppress, to some extent, neurasthenia and neurodegeneration.

For the TENS electrode needle in the embodiments of the present disclosure, the acupuncture point may be stimulated by the short-range closed-loop micro electric field formed after the needle bodies are energized, so it is able to promote cell metabolism, and return a potential at a nerve cell to a normal level at a lesion site. A nerve terminal may be electrically stimulated through the short-range electric field together with an acupuncture-therapy, so as to achieve a three-dimensional (3D) electric field effect therapy. In addition, the nerve terminal may be effectively stimulated in a closed-loop manner through the short-range electric field, and the current may be released through the two needle bodies in time, so it is able to perform the electrical stimulation within a relatively short time period, thereby to improve the adaptability of the human body to the current. Further, the current is released in time and merely transferred between the two needle bodies, so the other part(s) of the human body may not be adversely affected. As compared with the related art where the unidirectional pulse current is adopted, it is able to provide a larger current, thereby to improve the therapeutic effect.

Figure 3:
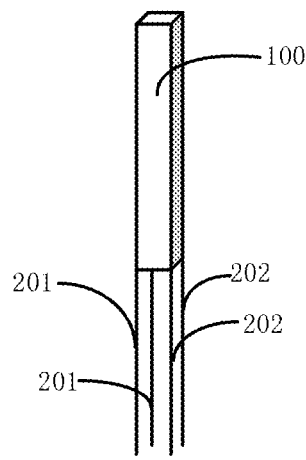
FIG. 3 is a schematic view showing the TENS electrode needle according to some embodiments of the present disclosure.

It should be appreciated that, for the TENS electrode needle in the embodiments of the present disclosure, the needle handle 100 may be made of a material such as ceramic, and the first electrode and the second electrode may be arranged within the needle handle 100. In a possible embodiment of the present disclosure, as shown in FIGS. 1 and 3, an electromagnetic coil 1001 may be wound onto the needle handle 100, and two ends of the electromagnetic coil 1001 may be connected to the first electrode and the second electrode respectively, so as to form an electromagnetic field in the case that the pulse current with opposite polarities are applied to the first electrode and the second electrode respectively. In this way, it is able to provide a better therapeutic effect under the effect of the electromagnetic field formed by the needle handle 100 and the current flowing through the needle bodies.

It should be appreciated that, for the TENS electrode needle in the embodiments of the present disclosure, the first electrode connected to the electromagnetic coil 1001 may be identical to, or different from, the first electrode connected to the first needle body 201. Identically, the second electrode connected to the electromagnetic coil 1001 may be identical to, or different from, the second electrode connected to the second needle body 202.

The needle bodies of the TENS electrode needle will be described hereinafter in conjunction with the embodiments.

First Embodiment

As shown in FIG. 1, the TENS electrode needle includes the needle handle 100 having the first electrode (not shown) and the second electrode (not shown) for providing the pulse current signals with different polarities are arranged; and the at least one first needle body 201 and the at least one second needle body 202 connected to the needle handle 100. Each of the first needle body 201 and the second needle body 202 includes the first end and the second end. The first end of the first needle body 201 is electrically connected to the first electrode, and the first end of the second needle body 202 is electrically connected to the second electrode. A length of the first needle body 201 is greater than a length of the second needle body 202, so as to form a longitudinal electrical field between the second end of the first needle body 201 and the second end of the second needle body 202.

In the case that an acupuncture operation is performed using the TENS electrode needle, the second end of the first needle body 201 having a greater length may be pierced into under the skin, and the second end of the second needle body 202 having a smaller length may be closely attached onto a surface of the skin. In the case that the pulse current signals with different polarities are applied to the first electrode and the second electrode respectively, the longitudinal electric field may be formed between the second end of the first needle body 201 and the second end of the second needle body 202.

In a possible embodiment of the present disclosure, as shown in FIG. 1, the second end of the first needle body 201 is of a pointed shape for piercing into the skin. The second end of the second needle body 202 includes an electrode ring 2020 attached onto the surface of the skin, and the first needle body 201 is inserted through the electrode ring 2020, so as to form the electrical field between the second end of the first needle body 201 and the electrode ring 2020 of the second needle body 202.

As mentioned above, the second end of the first needle body 201 having a greater length is of the pointed shape for piercing into under the skin, and the second end of the second needle body 202 having a smaller length is of an annular shape, e.g., a circular shape. During the acupuncture operation, the electrode ring 2020 of the second end of the second needle body 202 may be closely attached onto the surface of the skin. In the case that the pulse current signals with opposite polarities are applied to the first electrode and the second electrode respectively, the longitudinal electric field may be formed between the electrode ring 2020 attached onto the surface of the skin and the second end (a pointed end) of the first needle body 201 inserted through the electrode ring 2020.

In the case that the second end of the second needle body 202 is of the annular shape, it is able to, on one hand, reduce the damage to the surface of the skin, and on the other hand, increase a range of the longitudinal electric field formed between the first needle body 201 and the second needle body 202.

It should be appreciated that, the TENS electrode needle in the embodiments of the present disclosure may be applied to the part of the human body where the skin is relatively thick and the peripheral nerve is relatively insensitive. At this time, a slightly larger current, e.g., about 90 mA, may be applied.

In order to be adapted to different patients, in a possible embodiment of the present disclosure, at least one of the first needle body 201 and the second needle body 202 may be arranged on the needle handle 100 through a length adjustment mechanism, so as to adjust a length of the at least one of the first needle body and the second needle body extending out of the needle handle 100.

Through adjusting the length of the at least one of the first needle body 201 and the second needle body 202 extending out of the needle handle 100, it is able to adjust a longitudinal distance between the second end of the first needle body 201 and the electrode ring 2020 of the second needle body 202, so as to be adapted to different patients. In the case that the skin of the patient is relatively thick, it is necessary to provide a larger distance between the second end of the first needle body 201 and the electrode ring 2020 of the second needle body 202 through the length adjustment mechanism. In the case that the skin of the patient is relatively thin, it is necessary to provide a smaller distance between the second end of the first needle body 201 and the electrode ring 2020 of the second needle body 202 through the length adjustment mechanism.

In a possible embodiment of the present disclosure, the length adjustment mechanism may include: a movement passage arranged within the needle handle 100; a sliding block arranged within the movement passage, the first end of the at least one of the first needle body 201 and the second needle body 202 extending into the movement passage and being connected to the sliding block; and a delimiting mechanism configured to define a position of the sliding block.

A movement groove in communication with the movement passage may be provided in a peripheral portion of the needle handle 100, and the sliding block may protrude out of the movement groove, so as to facilitate the operation. In the case that it is necessary to adjust the length of the first needle body 201 and/or the second needle body 202, the sliding block may be pushed to move in the movement passage, so as to drive the second end of the first needle body 201 and/or the second needle body 202 to move. After the sliding block has moved to a predetermined position, the position of the sliding block may be defined by the delimiting mechanism. In this way, it is able to adjust the length of the first needle body 201 and/or the second needle body 202 extending out of the needle handle 100.

It should be appreciated that, although as mentioned above, the length adjustment mechanism may also be implemented in any other modes, which will not be particularly defined herein.

It should be further appreciated that, in a possible embodiment of the present disclosure, the first needle body 201 may be spaced apart from the second needle body 202 by a first distance in a range of about 0.2 mm to about 2 mm.

Second Embodiment

Figure 2:
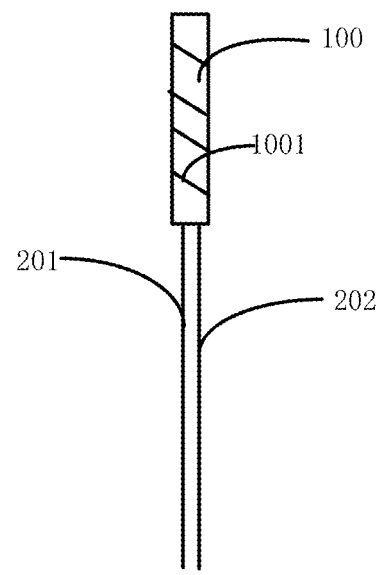
FIG. 2 is a schematic view showing a TENS electrode needle according to some embodiments of the present disclosure.

As shown in FIG. 2, the TENS electrode needle includes the needle handle 100 having the first electrode and the second electrode for providing the pulse current signals with different polarities are arranged; and the at least one first needle body 201 and the at least one second needle body 202 connected to the needle handle 100. Each of the first needle body 201 and the second needle body 202 includes the first end and the second end. The first end of the first needle body 201 is electrically connected to the first electrode, and the first end of the second needle body 202 is electrically connected to the second electrode. A length of the first needle body 201 is about the same as the second needle body 202, so as to generate a transverse electrical field between the second end of the first needle body 201 and the second end of the second needle body 202. In addition, each of the second ends of the first needle body 201 and the second needle body 202 is of a pointed shape.

In the case that an acupuncture operation is performed using the TENS electrode needle, both the second end of the first needle body 201 and the second end of the second needle body 202 may be pierced into under the skin. In the case that the pulse current signals with different polarities are applied to the first electrode and the second electrode respectively, the transverse electric field may be formed between the second end of the first needle body 201 and the second end of the second needle body 202. The TENS electrode needle in this embodiment may be used to stimulate a nerve at an acupuncture point.

It should be appreciated that, in order to be adapted to different patients, in a possible embodiment of the present disclosure, at least one of the first needle body 201 and the second needle body 202 may be arranged on the needle handle 100 through a length adjustment mechanism, so as to adjust a length of the at least one of the first needle body and the second needle body extending out of the needle handle 100.

Through adjusting the length of the at least one of the first needle body 201 and the second needle body 202 extending out of the needle handle 100, it is able to adjust a longitudinal distance between the second end of the first needle body 201 and the electrode ring 2020 of the second needle body 202, so as to be adapted to different patients. In the case that the skin of the patient is relatively thick, it is necessary to provide a larger distance between the second end of the first needle body 201 and the electrode ring 2020 of the second needle body 202 through the length adjustment mechanism. In the case that the skin of the patient is relatively thin, it is necessary to provide a smaller distance between the second end of the first needle body 201 and the electrode ring 2020 of the second needle body 202 through the length adjustment mechanism.

In a possible embodiment of the present disclosure, the length adjustment mechanism may include: a movement passage arranged within the needle handle 100; a sliding block arranged within the movement passage, the first end of the at least one of the first needle body 201 and the second needle body 202 extending into the movement passage and being connected to the sliding block; and a delimiting mechanism configured to define a position of the sliding block.

A movement groove in communication with the movement passage may be provided in a peripheral portion of the needle handle 100, and the sliding block may protrude out of the movement groove, so as to facilitate the operation. In the case that it is necessary to adjust the length of the first needle body 201 and/or the second needle body 202, the sliding block may be pushed to move in the movement passage, so as to drive the second end of the first needle body 201 and/or the second needle body 202 to move. After the sliding block has moved to a predetermined position, the position of the sliding block may be defined by the delimiting mechanism. In this way, it is able to adjust the length of the first needle body 201 and/or the second needle body 202 extending out of the needle handle 100.

It should be appreciated that, although as mentioned above, the length adjustment mechanism may also be implemented in any other modes, which will not be particularly defined herein.

It should be further appreciated that, in a possible embodiment of the present disclosure, the first needle body 201 may be spaced apart from the second needle body 202 by a first distance of 0.2 mm to 2 mm.

Third Embodiment

Figure 4:
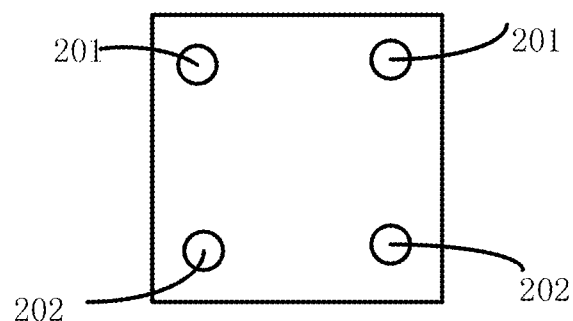
FIG. 4 is a bottom view of the TENS electrode needle in FIG. 3.

As shown in FIGS. 3 and 4, the TENS electrode needle includes the needle handle 100 having the first electrode and the second electrode for providing the pulse current signals with different polarities are arranged; and the at least one first needle body 201 and the at least one second needle body 202 connected to the needle handle 100. Each of the first needle body 201 and the second needle body 202 includes the first end and the second end. The first end of the first needle body 201 is electrically connected to the first electrode, and the first end of the second needle body 202 is electrically connected to the second electrode. One first needle body 201 and one second needle body 202 form one group, and at least two groups of needle bodies are arranged on the needle handle 100.

Through the at least two needle body groups on the needle handle 100, apart from the electric field formed between the needle bodies in each group, an additional electric field may also be formed between two adjacent needle bodies belonging to two groups respectively. During the acupuncture operation, it is able to form a composite electric field within the human body. In the case that the first needle body 201 and the second needle body 202 are made of metal alloys having different resistances, a resistance of a metal member located at a subcutaneous position may be increased, so as to provide a needle capable of generating heat. Through the cooperation of the needle capable of generating heat and the needle capable of releasing current, it is able to treat, to some extent, such pains as rheumatism and long-term typhoid fever.

In a possible embodiment of the present disclosure, as shown in FIGS. 3 and 4, orthographic projections of the at least two groups of needle bodies may be form vertices of a polygon of a polygonal form, e.g., a convex-polygonal form, onto a plane substantially perpendicular to the needle handle. The orthographic projections of the first needle body and the second needle body in each group may be form a pair of nonadjacent vertices of the polygon.

In the case that the two needle bodies in each group are arranged at the two positions diagonal to each other of the polygon respectively, during the acupuncture operation, it is able to form the composite electric field within the human body in a staggered manner and generate a thermal effect to some extent, thereby to relieve the rheumatic pain in a better manner.

As shown in FIGS. 3 and 4, there may be two groups of needle bodies arranged on the needle handle 100, and orthographic projections of the two groups of needle bodies onto the plane perpendicular to the needle handle form vertices of a diamond. The first needle body 201 and the second needle body 202 in each group may be respectively arranged at two positions diagonal to each other of the diamond.

It should be appreciated that, in some other embodiments of the present disclosure, more than two needle body groups may also be arranged on the needle handle 100. The orthographic projections of the first needle body and the second needle body belonging to a same group onto the plane perpendicular to the needle handle form a pair of nonadjacent vertices of the polygon e.g., they may be respectively arranged at the two positions diagonal to each other of the polygon. In the case that there are three needle body groups, they may be arranged in a hexagonal form, and the first needle body 201 and the second needle body 202 in the same group may be arranged at two positions diagonal to each other of a hexagon.

It should be further appreciated that, as mentioned above, there are an even number of needle bodies on the needle handle 100. However, in some other embodiments of the present disclosure, an odd number of needle bodies may also be arranged on the needle handle 100, at least including one first needle body 201 and one second needle body 202. For example, three needle bodies may be arranged on the needle handle 100, including two first needle bodies 201 and one second needle body 202. The second needle body 202 may be arranged between the two first needle bodies 201, so as to generate the short-range electric field between the second needle body 202 and each of the two first needle bodies 201. For example, in the case that two first needle bodies and one second needle body are arranged on the needle handle, a distance between the second needle body and any one of the two first needle bodies is smaller than a distance between the two first needle bodies. The three needle bodies may be arranged along a straight line or in a triangular form on the plane perpendicular to the needle handle.

Figure 5:
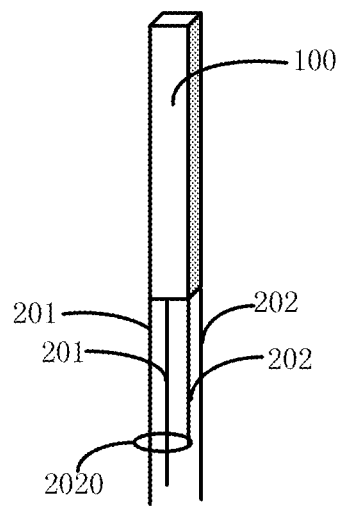
FIG. 5 is a schematic view showing a TENS electrode needle according to some embodiments of the present disclosure.

It should be further appreciated that, the first needle body 201 and the second needle body 202 in each group in this embodiment may be those mentioned in the first embodiment, or those mentioned in the second embodiment. In addition, as shown in FIG. 5, at least one group of needle bodies may include the first needle body 201 and the second needle body 202 mentioned in the first embodiment, and at least another group of needle bodies may include the first needle body 201 and the second needle body 202 mentioned in the second embodiment.

In addition, in this embodiment, in the at least two groups of needle bodies, orthographic projections of two needle bodies in the at least two groups onto the plane perpendicular to the needle handle, which form two adjacent vertices of the polygon, are spaced apart from each other at a second distance in a range of about 0.2 mm to about 2 mm.

In order to be adapted to different patients, in a possible embodiment of the present disclosure, at least one of the first needle body 201 and the second needle body 202 may be arranged on the needle handle 100 through a length adjustment mechanism, so as to adjust a length of the at least one of the first needle body and the second needle body extending out of the needle handle 100.

Through adjusting the length of the at least one of the first needle body 201 and the second needle body 202 extending out of the needle handle 100, it is able to adjust a longitudinal distance between the second end of the first needle body 201 and the electrode ring 2020 of the second needle body 202, so as to be adapted to different patients. In the case that the skin of the patient is relatively thick, it is necessary to provide a larger distance between the second end of the first needle body 201 and the electrode ring 2020 of the second needle body 202 through the length adjustment mechanism. In the case that the skin of the patient is relatively thin, it is necessary to provide a smaller distance between the second end of the first needle body 201 and the electrode ring 2020 of the second needle body 202 through the length adjustment mechanism.

In a possible embodiment of the present disclosure, the length adjustment mechanism may include: a movement passage arranged within the needle handle 100; a sliding block arranged within the movement passage, the first end of the at least one of the first needle body 201 and the second needle body 202 extending into the movement passage and being connected to the sliding block; and a delimiting mechanism configured to define a position of the sliding block.

A movement groove in communication with the movement passage may be provided in a peripheral portion of the needle handle 100, and the sliding block may protrude out of the movement groove, so as to facilitate the operation. In the case that it is necessary to adjust the length of at least one of the first needle body 201 and the second needle body 202, the sliding block may be pushed to move in the movement passage, so as to drive the second end of at least one of the first needle body 201 and the second needle body 202 to move. After the sliding block has moved to a predetermined position, the position of the sliding block may be defined by the delimiting mechanism. In this way, it is able to adjust the length of at least one of the first needle body 201 and the second needle body 202 extending out of the needle handle 100.

It should be appreciated that, although as mentioned above, the length adjustment mechanism may also be implemented in any other modes, which will not be particularly defined herein.

Figure 6:
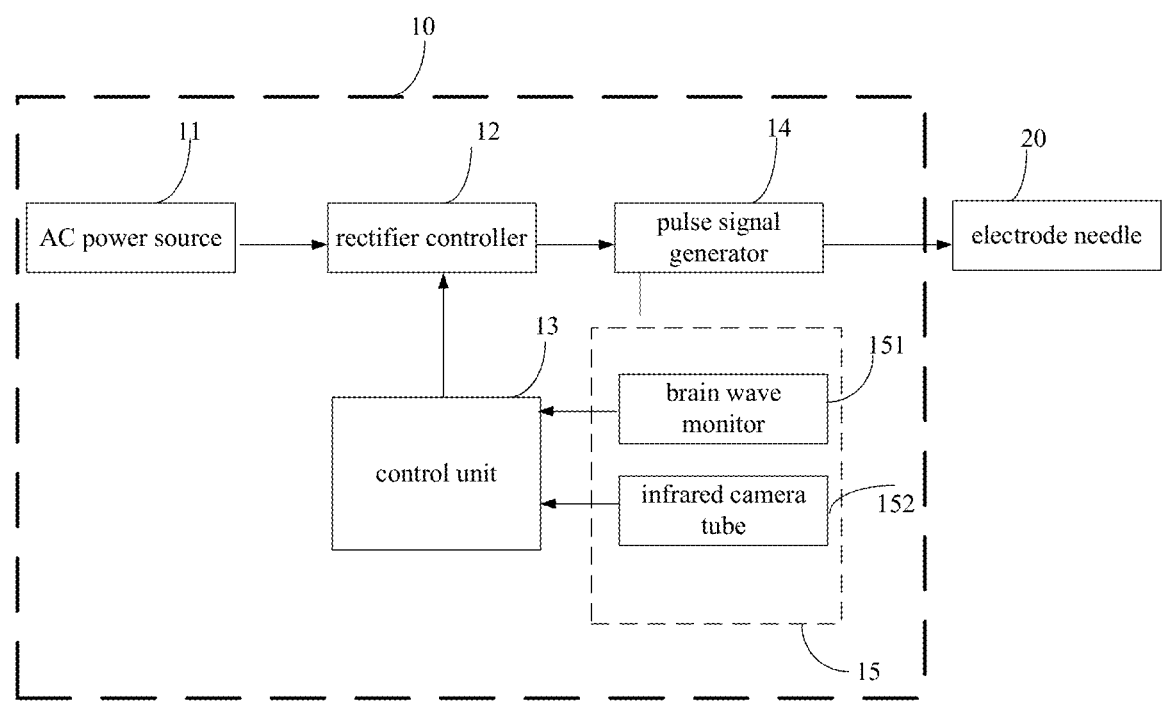
FIG. 6 is a block diagram of a TENS device according to some embodiments of the present disclosure.

As shown in FIG. 6, the present disclosure further provides in some embodiments a TENS device, which includes: a pulse signal generation mechanism 10 having two output ends for outputting pulse current signals with different polarities; and any one of the above-mentioned TENS electrode needles 20. The first electrode and the second electrode in the needle handle 100 of the TENS electrode needle 20 are electrically connected to the two output ends of the pulse signal generation mechanism 10 respectively.

The electrode needle adopted by the TENS device is just any one the above-mentioned TENS electrode needles. The pulse current signals with opposite polarities may be applied by the pulse signal generation mechanism 10 to the first electrode and the second electrode on the needle handle 100 respectively. The pulse signal generation mechanism may generate a pulse current at a certain period, and the pulse current flows into the first electrode in the needle handle 100 and out of the second electrode. In use, the second end of at least one of the first needle body 201 and the second needle body 202 may be pierced into under the epidermis. At this time, a short-range closed-loop micro electric field may be formed between the second ends of the two needle bodies arranged very close to each other, so as to change a micro electric field at an acupuncture point, thereby to stimulate the relevant acupuncture point. In addition, the nerve terminal may be effectively stimulated in a closed-loop manner through the short-range electric field, and the current may be released through the two needle bodies in time, so it is able to perform the electrical stimulation within a relatively short time period, thereby to improve the adaptability of the human body to the current. Further, the current is released in time and merely transferred between the two needle bodies, so the other parts of the human body may not be adversely affected. As compared with the related art where the unidirectional pulse current is adopted, it is able to provide a larger current, thereby to improve the therapeutic effect.

As shown in FIG. 6, the pulse signal generation mechanism 10 includes: a power source 11 configured to provide an alternate current; a rectifier controller 12 connected to the power source 11 and configured to output a sinusoidal current; a control unit 13 connected to the rectifier controller 12 and configured to control an output state of the sinusoidal current from the rectifier controller 12, the output state including an output frequency and a magnitude of the sinusoidal current; and a pulse signal generator 14 connected to the rectifier controller 12 and configured to receive the sinusoidal current from the rectifier controller 12 and generate the pulse current signal.

According to the TENS device in the embodiments of the present disclosure, the rectifier controller 12 is powered via an alternate current (AC) power source 11, and then applies the sinusoidal current to the pulse signal generator 14. Fluctuation of the pulse current may be controlled by changing an input frequency of the sinusoidal current, and a magnitude of the pulse current may be controlled by changing the magnitude of the sinusoidal current. The pulse signal generator 14 may be connected to the TENS electrode needle, and a current may be formed between the first needle body 201 and the second needle body 202 of the TENS electrode needle due to a field effect.

In a possible embodiment of the present disclosure, as shown in FIG. 6, the pulse signal generation mechanism 10 further includes an obtaining unit 15 configured to obtain feedback information of a patient stimulated by a current predetermined pulse current signal. The control unit 13 is further connected to the obtaining unit 15 and configured to control the output state of the sinusoidal current from the rectifier controller 12 in accordance with the feedback information obtained by the obtaining unit 15.

The electrical stimulation may be performed on the patient through the predetermined pulse current signal. The feedback information about the patient may be monitored in real time by the obtaining unit 15. Then, the control unit 13 may control the rectifier controller 12 in accordance with the feedback information obtained by the obtaining unit 15, so as to generate the current at a corresponding intensity, thereby to adjust the intensity of the pulse current in accordance with the adaptability of the human body. In this way, it is able to determine the intensity of the pulse current with respect to different patients.

In a possible embodiment of the present disclosure, as shown in FIG. 6, the obtaining unit 15 includes: a brain wave monitor 151 configured to obtain a brain wave signal of the patient stimulated by the current predetermined pulse current signal, generate a first feedback signal and transmit the first feedback signal to the control unit 13; and/or an infrared camera tube 152 configured to obtain a state of a skin surface of the patient stimulated by the current predetermined pulse current signal corresponding to a position where the TENS electrode needle is located, generate a second feedback signal and transmit the second feedback signal to the control unit 13.

The brain wave monitor 151 may monitor at any time the brain wave signal of the patient stimulated by the current predetermined pulse current signal, so as to monitor an endurance degree of the patient. Then, the rectifier controller 12 may control the pulse signal generator 14 in accordance with the brain wave signal monitored by the brain wave monitor 151, so as to change the pulse current, thereby to obtain the pulse current signal adapted to the current patient.

In addition, the infrared camera tube 152 may monitor at any time the state of the skin surface of the patient stimulated by the current predetermined pulse current signal corresponding to the position where the TENS electrode needle is located so as to monitor the endurance degree of the patient. Then, the rectifier controller 12 may control the pulse signal generator 14 in accordance with the state of the skin surface (e.g., a temperature of the skin) monitored by the infrared camera tube 152, so as to change the pulse current, thereby to obtain the pulse current signal adapted to the current patient.

The pulse current may be treated by the rectifier controller 12 and then applied to the nerve in the skin from weak to strong gradually. During the application, the brain wave monitor 151 may monitor the brain wave signal of the patient, and the infrared camera tube 152 may monitor the temperature of the skin (i.e., a change in the temperature of the skin at the position where the TENS electrode needle is located), so as to adjust the magnitude of the current with respect to the patient.

It should be appreciated that, in some other embodiments of the present disclosure, apart from the brain wave monitor 151 and the infrared camera tube 152, the obtaining unit 15 may also be implemented in another ways, which will not be particularly defined herein.

It should be further appreciated that, the control unit 13 in the TENS device may be a Procedural Language (PL) control unit, which may also be provided with a memory for storing therein the current predetermined pulse current signal in the case that the predetermined feedback information about the patient is obtained and within a certain range. For example, in the case that the electrical stimulation is performed on an identical patient for the second time, the stored predetermined pulse current signal may be directly used.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A transcutaneous electrical nerve stimulation (TENS) electrode needle, comprising:
    a needle handle having a first electrode and a second electrode for providing pulse current signals with different polarities; and
    at least one first needle body and at least one second needle body;
    wherein each of the first needle body and the second needle body comprises a first end and a second end; and
    wherein the first end of the first needle body is electrically connected to the first electrode, and the first end of the second needle body is electrically connected to the second electrode, so as to form an electrical field between the second end of the first needle body and the second end of the second needle body; and
    wherein at least one of the first needle body or the second needle body is arranged on the needle handle through a length adjustment mechanism, so as to adjust a length of the at least one of the first needle body or the second needle body extending out of the needle handle.

2. The TENS electrode needle according to claim 1, wherein a length of the first needle body is greater than a length of the second needle body.

3. The TENS electrode needle according to claim 2, wherein:
    the second end of the first needle body is of a pointed shape for piercing into skin; and
    the second end of the second needle body comprises an electrode ring attached onto a surface of the skin, and the first needle body is inserted through the electrode ring, so as to form the electrical field between the second end of the first needle body and the electrode ring of the second needle body.

4. The TENS electrode needle according to claim 1, wherein a length of the first needle body is about the same as that of the second needle body, and each of the second end of the first needle body and the second end of the second needle body is of a pointed shape.

5. The TENS electrode needle according to claim 1, wherein at least two groups of needle bodies are arranged on the needle handle, and each group comprises one of the at least one first needle body and one of the at least one second needle body.

6. The TENS electrode needle according to claim 5, wherein orthographic projections of the at least two groups of needle bodies onto a plane perpendicular to the needle handle form vertices of a polygon.

7. The TENS electrode needle according to claim 6, wherein the polygon comprises a convex polygon.

8. The TENS electrode needle according to claim 7, wherein the at least two groups of needle bodies comprises two groups of needle bodies that are arranged on the needle handle, and orthographic projections of the two groups of needle bodies onto the plane perpendicular to the needle handle form vertices of a diamond.

9. The TENS electrode needle according to claim 6, wherein orthographic projections of the first needle body and the second needle body belonging to a same group onto the plane perpendicular to the needle handle form a pair of nonadjacent vertices of the polygon.

10. The TENS electrode needle according to claim 6, wherein orthographic projections of two needle bodies in the at least two groups onto the plane perpendicular to the needle handle, which form two adjacent vertices of the polygon, are spaced apart from each other at a distance in a range of about 0.2 mm to about 2 mm.

11. The TENS electrode needle according to claim 1, wherein the at least one first needle body comprises two first needle bodies and the at least one second needle body comprises one second needle body, the two first needle bodies and the second needle body are arranged on the needle handle, and a distance between the second needle body and any one of the two first needle bodies is smaller than a distance between the two first needle bodies.

12. The TENS electrode needle according to claim 1, wherein a distance between any one of the at least one first needle body and any one of the at least one second needle body ranges from about 0.2 mm to about 2 mm.

13. The TENS electrode needle according to claim 1, wherein the first needle body has a resistance different from the second needle body.

14. The TENS electrode needle according to claim 1, wherein the length adjustment mechanism comprises:
  a movement passage arranged within the needle handle;
  a sliding block arranged within the movement passage, the first end of the at least one of the first needle body and the second needle body extending into the movement passage and being connected to the sliding block; and
  a delimiting mechanism configured to define a position of the sliding block.

15. The TENS electrode needle according to claim 1, wherein an electromagnetic coil is wound onto the needle handle, and first and second ends of the electromagnetic coil are electrically connected to the first electrode and the second electrode respectively.

16. A transcutaneous electrical nerve stimulation (TENS) device, comprising:
  a pulse signal generation mechanism having two output ends for outputting pulse current signals with different polarities; and
  the TENS electrode needle according to claim 1,
  wherein the first electrode and the second electrode in the needle handle of the TENS electrode needle are electrically connected to the two output ends of the pulse signal generation mechanism respectively.

17. The TENS device according to claim 16, wherein the pulse signal generation mechanism comprises:
  a power source configured to provide an alternate current;
  a rectifier controller connected to the power source and configured to output a sinusoidal current;
  a control unit connected to the rectifier controller and configured to control an output state of the sinusoidal current from the rectifier controller, wherein the output state comprises an output frequency and a size of the sinusoidal current; and
  a pulse signal generator connected to the rectifier controller and configured to receive the sinusoidal current from the rectifier controller and generate the pulse current signals.

18. The TENS device according to claim 17, wherein the pulse signal generation mechanism further comprises an obtaining unit configured to obtain feedback information of a patient stimulated by a current predetermined pulse current signal, and the control unit is further connected to the obtaining unit and configured to control the output state of the sinusoidal current from the rectifier controller in accordance with the feedback information obtained by the obtaining unit.

19. The TENS device according to claim 18, wherein the obtaining unit comprises:
  a brain wave monitor configured to obtain a brain wave signal of the patient stimulated by the current predetermined pulse current signal, generate a first feedback signal and transmit the first feedback signal to the control unit;
  and/or an infrared camera tube configured to obtain a state of a skin surface of the patient stimulated by the current predetermined pulse current signal at a position where the TENS electrode needle is located, generate a second feedback signal and transmit the second feedback signal to the control unit.

* * * * *